US005399162A

United States Patent [19]

Cselle

[11] Patent Number: 5,399,162

[45] Date of Patent: Mar. 21, 1995

[54] AUTOMATIC BALLING GUN

[76] Inventor: Edward Cselle, P.O. Box 451, Northfield, Ohio 44067

[21] Appl. No.: 200,602

[22] Filed: Feb. 23, 1994

[51] Int. Cl.$^{6}$ .......... A61M 31/00

[52] U.S. Cl. .......... 604/60

[58] Field of Search .......... 604/15, 59-64, 604/73, 135

[56] References Cited

U.S. PATENT DOCUMENTS

| | | | |
|---|---|---|---|
| 17,000 | 4/1857 | Somerrille | 604/59 |
| 139,856 | 6/1873 | Bex | 604/59 |
| 453,508 | 6/1891 | Ruby . | |
| 842,631 | 1/1907 | Deperdussin | 604/63 |
| 2,017,783 | 10/1935 | Clark . | |
| 2,650,593 | 9/1953 | Weil et al. . | |
| 4,474,308 | 10/1984 | Bergeron | 604/59 |
| 5,281,197 | 1/1994 | Arias et al. | 604/60 |
| 5,284,479 | 2/1994 | de Jong | 604/63 |

FOREIGN PATENT DOCUMENTS

| | | | |
|---|---|---|---|
| 1190 | of 1895 | United Kingdom | 604/59 |

*Primary Examiner*—John D. Yasko
*Attorney, Agent, or Firm*—Christopher W. Brody

[57] ABSTRACT

An automatic balling gun includes an elongated member having a tubular profile which is easily operated and manipulated by the single hand of the user. A release assembly is mounted along the length of the tubular member to dispense medicine orally to an animal by merely depressing a plunger. A knob is provided on a proximal end of the automatic balling gun which facilitates cocking the gun and loading a dispensing chamber thereof with a capsule or pill to be dispensed. The automatic balling gun can then be inserted into the animal to be treated followed by depressing the plunger on the release assembly to dispense the medication from the gun.

15 Claims, 2 Drawing Sheets

AUTOMATIC BALLING GUN

FIELD OF THE INVENTION

The present invention is directed to an automatic balling gun for dispensing oral medication to animals and, in particular, to a balling gun having a tubular profile with a release mechanism facilitating manipulation of the gun and dispensing of the oral medication.

BACKGROUND ART

Various devices have been proposed to administer or dispense capsules or other types of oral medication to animals. One device includes a tube having a pill holding chamber on one end with a pair of gripping rings on the opposite end. The tube has a rod mounted therethrough, one end designed to force the pill from the pill chamber by manually forcing the opposite end of the rod through the tube. This device is cumbersome in that it requires two hands to manipulate and dispense the pill. In addition, manual sliding of the rod does not always provide sufficient force to inject the pill down an animal's throat.

Other dispensing devices use a spring mechanism to eject or dispense the oral medication. U.S. Pat. No. 2,650,593 to Weil et al. discloses a balling gun which automatically cocks upon insertion of a capsule into the gun. The balling gun has a pistol grip on one end and has a complicated firing mechanism requiring rotation of a tube and interaction between the tube and a conical projection on an adjacent rod.

U.S. Pat. No. 2,017,783 to Clark discloses a capsule administering device including a duck-bill clamp which retains a capsule in a desired position prior to insertion of the instrument into the throat of an animal. The duck-bill clamp opens to permit dispensing of the capsule under action of a spring.

U.S. Pat. No. 453,508 to Ruby also discloses a veterinary instrument having a clamp like distal end and a pistol grip at the proximal end for administering a capsule to an animal. This instrument has a capsule clamping device which is spring biased and released by a trigger mechanism.

One disadvantage of the prior art devices disclosed above includes a complex mechanism to dispense capsules or a medication to animals, the mechanism requiring many moving parts. In addition, certain prior art devices are difficult to simultaneously manipulate and dispense the medication and have high manufacturing costs.

In response to these drawbacks, a need has developed to provide a simple, low cost and easily manipulating balling gun for dispensing of oral medication to animals.

In response to this need, the present invention provides an automatic balling gun having a slim tubular profile which is simple to use, low in cost and easily manipulated to dispense medication to an animal.

SUMMARY OF THE INVENTION

Accordingly, it is a first object of the present invention to provide an improved automatic balling gun to dispense oral medication to animals.

Another object of the present invention is to provide a balling gun which is easy to use by requiring only a single hand to both position the gun and dispense medication to an animal.

A further object of the present invention is to provide a balling gun having a design which is easily adaptable for different animals and different types of medication.

Other objects and advantages of the present invention will become apparent as a description thereof proceeds.

In satisfaction of the foregoing objects and advantages, the present invention provides an automatic balling gun for dispensing medicine orally to an animal comprising an elongated hollow member having distal and proximal ends. A rod is disposed within the hollow member extending along an axis thereof and includes a reduced diameter portion. The rod also has a cap at one end, a knob at the other end, the rod being spring biased toward the distal end of the hollow member to dispense a capsule or the like to an animal.

A release assembly is also provided, a portion thereof mounted within the elongated hollow member and spaced between the distal and proximal ends thereof. The release assembly includes a sleeve having an open top, closed bottom and a pair of aligned apertures in a side wall thereof. The sleeve is mounted within the elongated hollow member with the rod extending through the aligned apertures. The release assembly also includes a plunger having a first cylindrical portion sized to slidably engage the sleeve, the cylindrical portion having a bore therethrough and a recess at one end thereof. Adjacent the cylindrical portion is a second rounded portion sized to seat against the open top of the sleeve and provide a surface for activating the release assembly. A spring is arranged in the sleeve for engagement with the recess to spring bias the plunger upwardly with respect to the sleeve bottom.

In operation, the knob of the rod at the proximal end of the hollow member is pulled to retract the rod so that the automatic balling gun is cocked. The rod remains in the cocked position by the spring biasing of the plunger upwardly such that the bore in the first cylindrical portion engages the reduced diameter portion of the rod. Depression of the plunger aligns the apertures of the sleeve with the bore so that the rod is propelled toward the distal end of the hollow member. Any capsule positioned in the distal end chamber of the hollow member is dispensed by the cap of the rod contacting the capsule and projecting it into the throat of an animal.

The rod also includes a stop member therearound which engages a shoulder in the hollow member to limit rod travel and spring compression when the gun is being cocked.

BRIEF DESCRIPTION OF DRAWINGS

Reference is now made to the drawings accompanying the invention wherein.

DESCRIPTION OF THE PREFERRED EMBODIMENTS

The present invention offers advantages over other prior art balling guns by providing a sleek tubular profile which is easy to manipulate and operate when dispensing oral medication to an animal. Simple cocking of the automatic balling gun with a finger touch release mechanism allows a user to insert the balling gun into the throat of an animal and dispense the desired medication with one hand.

The inventive automatic balling gun provides an improved release assembly which minimizes manufacturing costs and provides a reliable and durable mechanism to provide consistent and long term use of the balling gun for its desired purpose.

Figure 1:
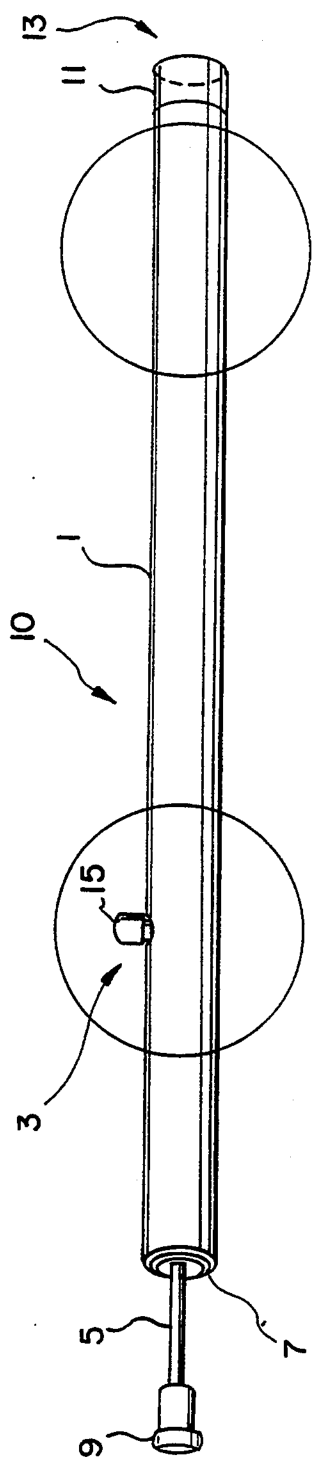
FIG. 1 is a perspective view of the automatic balling gun.

With reference now to FIG. 1, the inventive automatic balling gun is generally designated by the reference numeral 10 and includes a tube 1, a release mechanism 3, a rod 5 extending along the axis of the tube 1 and an end cap 7. The rod 5 has a knob 9 on the proximal end thereof to facilitate cocking the automatic balling gun as will be described herein below. The distal end of the tube 1 can also have a resilient covering 11 to protect an animal when inserting the tube into a throat thereof.

In use, the knob 9 is pulled back into a cocked position as shown in FIG. 1 and a pill, capsule or other type of oral medicine (not shown) is inserted into a dispensing chamber 13 at the distal end of the tube 1. Depression of the plunger 15 of the release assembly releases the rod 5 such that a spring bias propels the rod 5 toward the distal end of the tube to dispense a capsule into the throat of an animal.

Figure 2:
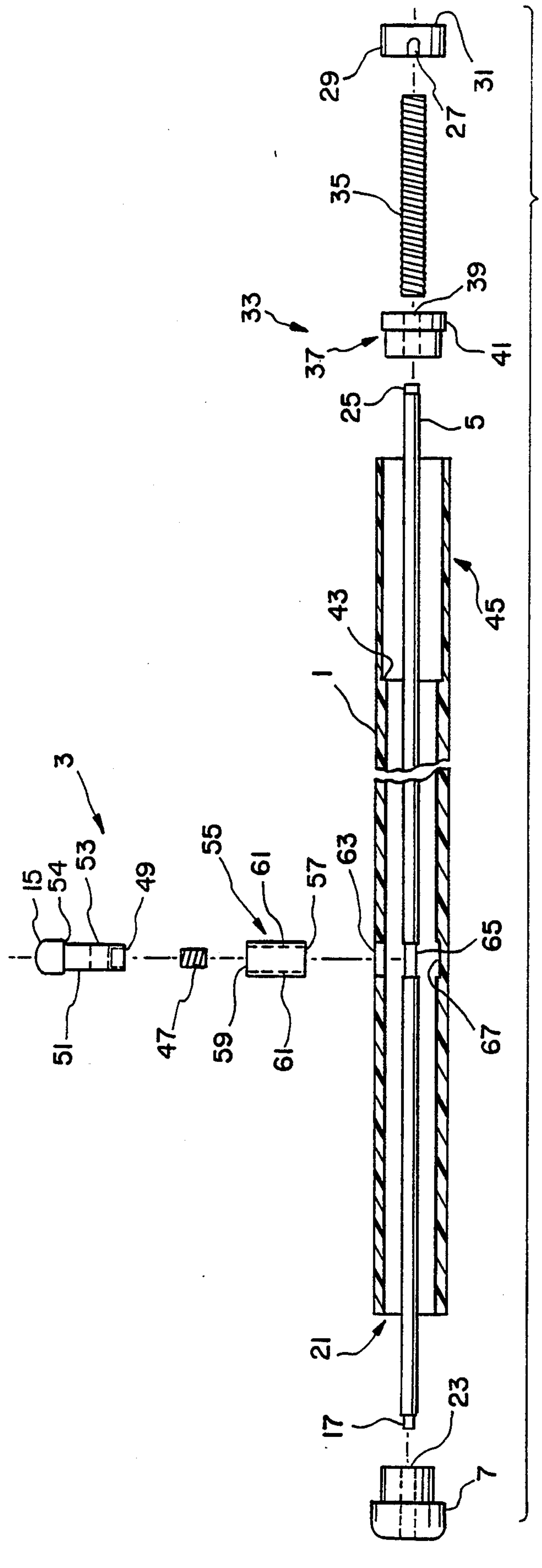
FIG. 2 is a exploded side view of the balling gun showing individual components thereof.

With reference now to FIG. 2, the rod 5 has opposing threaded ends, one end 17 adapted to attach to knob 9 by a complementary threaded recess 19 therein. The end cap 7 is sized to seat against the proximal end 21 of the tube. The end cap 7 also has a bore 23 which permits passage of the rod 5 therethrough for attachment to the knob 9.

The other end of the rod 25 is also threaded and designed to engage a complementary threaded recess 27 in the cap 29. The surface 31 of the cap 29 forms part of the oral medicine or pill receiving chamber 13 (FIG. 1) for propulsion of a capsule thereof when the automatic balling gun is operated.

FIG. 2 also discloses a spring biasing mechanism 33 which includes the cap 29, a coil spring 35 and a stop 37. The stop 37 has a through bore 39 which permits passage of the rod 55 for attachment to the cap 31. The stop 37 has an enlarged diameter portion 41 which seats against the shoulder 43 formed in the inner tube by the enlarged diameter portion 45 thereof. The stop 37 provides a stationary surface against which the coil spring 35 can be compressed when the automatic balling gun is cocked.

The release mechanism 3, besides including the plunger 15 also has a coil spring 47 sized to engage a recess 49 in the portion 51 of the plunger 15. The portion 51 also includes a bore 53 therethrough. The function of the bore will be described hereinafter. The plunger 15 is rounded at the top to facilitate depression when activating the release assembly. The plunger also has a step 54 which seats against a sleeve 55 to limit plunger travel. The sleeve 55 has a closed bottom 57 and an open top 59. The sleeve includes a pair of aligned apertures 61 which cooperate with the bore 53 and spring 47 to control the spring biasing mechanism 33. The portion 51 of the plunger 15, the coil spring 47 and sleeve 55 mount within the circular opening 63 in the tube 1.

When these components are mounted within tube 1, the rod 5 extends through the aligned apertures 61 and bore 53. The rod includes a reduced diameter portion 65 which interacts with the release assembly to hold the rod in a cocked position.

The tube 1 may also have a recess 67 to seat the bottom 57 of the sleeve when inserted therein.

Figure 3B:
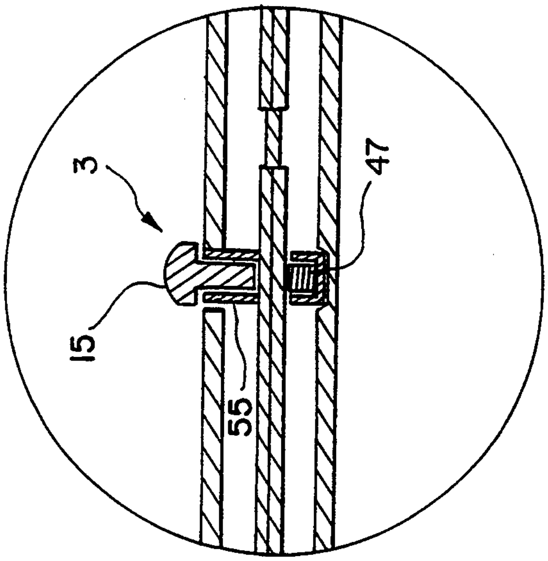
FIGS. 3A and 3B show portions of FIG. 1 enlarged to show greater detail representing cocked and released positions of the balling gun.
Figure 3A:
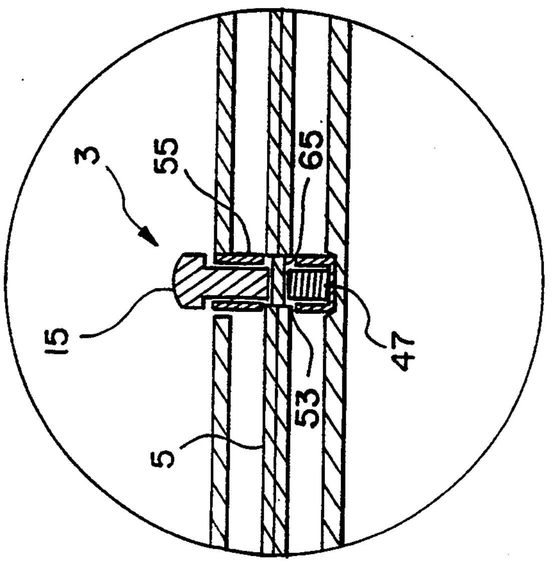

With reference now to FIGS. 1 and 3, the release mechanism 3 is shown in greater detail. FIG. 3A depicts the rod in the cocked position with the release mechanism interacting with the reduced diameter portion 65 of the rod to retain the rod in the cocked position. In the cocked position, the plunger 15 is biased upwardly by the coil spring 47. By the spring bias of the coil spring 47, the bore 53 of the plunger seats against the reduced diameter portion 65 of the rod 5. Thus, although the rod 5 is aligned with the apertures 61 of the sleeve, the plunger, by seating against the reduced diameter portion 65, prevents travel of the rod. When the rod 5 is retracted by pulling on the knob 9, the reduced diameter portion 65 translates from the position shown in FIG. 3B to that shown in FIG. 3A to lock the rod in place.

Still with reference to FIG. 3B, depression of the plunger 15 acts against the spring bias of the spring 47 so that the bore 53 of the plunger and the apertures 61 of the sleeve are coincident. Once this coincidence is achieved, the rod 5 is free to travel through the sleeve apertures and the plunger bore. Since the spring 35 is compressed when the rod is in the cocked position, see FIG. 3A, release of the reduced diameter portion 65 of the rod allows the spring 35 to expand against the cap 29 and translate the rod. 5 towards the distal end of the tube 1 to dispense any medication therein.

The rod can then be recocked, followed by insertion of the desired medication and dispensing thereof by depressing the plunger 15.

Figure 4:
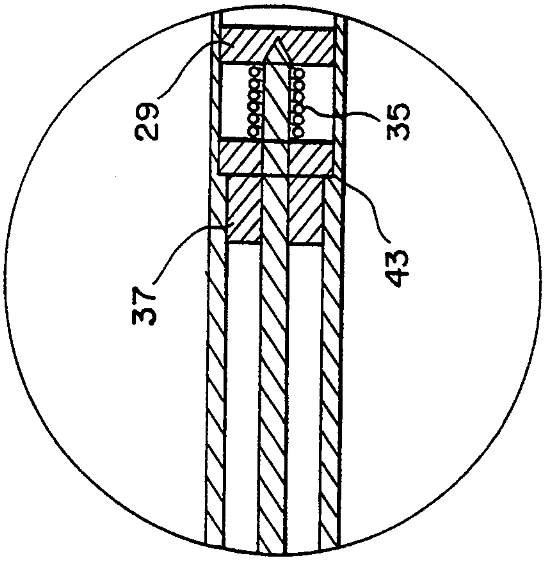
FIG. 4 shows another portion of FIG. 1 enlarged to show greater detail of the spring biasing mechanism of the balling gun.

With reference to FIG. 4, the spring bias mechanism is shown in the compressed state. That is, the stop 37 is shown seated against the shoulder 43 with the spring 35 compressed between the stop 37 and the cap 29.

Figure 5:
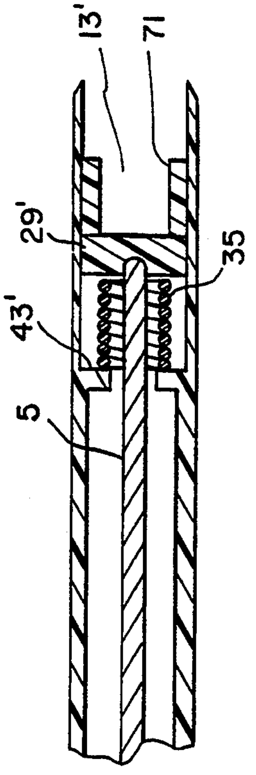
FIG. 5 is similar to FIG. 4 showing an alternative embodiment.

In an alternative embodiment, with reference to FIG. 5, the stop 37 can be replaced with an enlarged shoulder 43'. The enlarged shoulder 43' provides a stop against the spring 35 when compressed by cocking of the rod 5. Additionally, a cap 29' can be provided which is cup-shaped by the addition of the sidewall 71. With this cap, a smaller dispensing chamber 13' is provided to accommodate smaller sized capsules or pills for dispensing. Of course, the cap 29' can also be used in the embodiment depicted in FIG. 4.

The release assembly, although located closer to the proximal end of the tube 1, can be positioned along any portion of the length of tube 1. In certain applications, it may be more desirable to have the release assembly closer to the knob 9, for example, when shorter tubes are used for smaller animals. Different diameter tubes may also be utilized depending on the animal intended to be treated.

The knob 9 may also have a washer or other resilient means disposed between the end cap 7 and knob 9. The washer facilitates absorption of the impact of the knob against the end cap during dispensing.

Preferably, the tube, knob, end cap, stop and cap are made of a non-metallic material such as a polymer, for example, ABS, polyvinylchloride, high density polyethylene or the like. The release assembly and rod are preferably made of a metallic material to provide durability and long life for the automatic balling gun.

As such, an invention has been disclosed in terms of preferred embodiments thereof which fulfill each and every one of the objects of the present invention as set forth hereinabove and provide a new and improved automatic balling gun for dispensing medicine orally to animals.

Various changes, modifications and alterations from the teaching of the present invention may be contemplated by those skilled in the art without departing from the intended spirit and scope thereof. Accordingly, it is intended that the present invention only be limited by the terms of the appended claims.

I claim:

1. An automatic balling gun for dispensing medicine orally to an animal comprising:

a) an elongated hollow member having a distal and a proximal end and an enlarged diameter portion extending from the distal end of said elongated hollow member and terminating at a stop;

b) a rod extending along an axis of said elongated hollow member, said rod having a reduced diameter portion, a cap at one end thereof and a knob at the other end, and a spring surrounding said rod and disposed between said stop and said cap to spring bias said cap and rod towards said distal end when said release assembly releases said reduced diameter portion of said rod; and c) a release assembly, a first portion thereof mounted within said elongated hollow member with a second portion extending through a sidewall of said elongated hollow member and spaced between said distal and proximal ends, d) wherein said release assembly holds said reduced diameter portion of said rod in a cocked position and releases said portion from said cocked position to dispense said medicine by said spring bias.

2. The automatic balling gun of claim 1 wherein said stop is integral with said elongated hollow member.

3. The automatic balling gun of claim 1 further comprising a resilient covering surrounding a distal end of said elongated tube.

4. The automatic balling gun of claim 1 wherein said elongated hollow member is cylindrical in shape.

5. The automatic balling gun of claim 1 wherein said elongated hollow member has a cap on said proximal end with a bore therethrough to receive said rod.

6. An automatic balling gun for dispensing medicine orally to an animal comprising:

a) an elongated hollow member having a distal and a proximal end; and b) a rod extending along an axis of said elongated hollow member, said rod having a reduced diameter portion, a cap at one end thereof and a knob at the other end, said rod being biased by a spring toward said distal end to dispense said medicine; and c) a release assembly, a portion thereof mounted within said elongated hollow member and spaced between said distal and proximal ends, d) wherein said release assembly holds a said portion of said rod in a cocked position and releases said portion from said cocked position to dispense said medicine by said spring bias, said release assembly further comprising:

i) a sleeve having an open top, closed bottom and a pair of aligned apertures in a sidewall thereof, said sleeve mounted within said elongated hollow member;

ii) a cylindrical plunger having a first portion sized to engage said sleeve, said first portion having a bore therethrough, and a recess at a free end thereof, and a second portion opposite said free end and sized to seat against said open top of said sleeve; and iii) a second spring arranged in said sleeve for engagement with said recess to spring bias said plunger upwardly with respect to said sleeve bottom;

iv) wherein depression of said plunger aligns said apertures and said bore to release said portion of said rod from said cocked position.

7. An automatic balling gun for dispensing medicine comprising:

a) an elongated hollow member having a distal and a proximal end;

b) a rod extending along an axis of said elongated hollow member, said rod having a cap at one end thereof and a knob at the other end, said rod being biased by a first spring toward said distal end to dispense said medicine; and c) a release assembly, a portion thereof mounted within said elongated hollow member and spaced between said distal and proximal ends, said release assembly holding a portion of said rod in a cocked position and for releasing said portion from said cocked position to dispense said medicine by said spring bias, said release assembly further comprising:

i) a sleeve having an open top, closed bottom and a pair of aligned apertures in a sidewall thereof, said sleeve mounted within said elongated hollow member;

ii) a cylindrical plunger having a first portion sized to engage said sleeve, said first portion having a bore therethrough and a recess at a free end thereof, and a second portion opposite said free end and sized to seat against said open top of said sleeve; and iii) a second spring arranged in said sleeve for engagement with said recess to spring bias said plunger upwardly with respect to said sleeve bottom;

iv) wherein depression of said plunger aligns said apertures and said bore to release said portion of said rod from said cocked position to dispense said medicine.

8. The automatic balling gun of claim 7 further comprising:

i) an enlarged diameter portion extending from a distal end of said elongated hollow member and terminating at a step;

ii) a stop disposed within said enlarged diameter portion adjacent said step and surrounding said rod;

iii) said second spring surrounding said rod and disposed between said stop and said cap to spring bias said cap towards said distal end when said release assembly releases said portion of said rod.

9. The automatic balling gun of claim 7 further comprising a resilient covering surrounding a distal end of said elongated tube.

10. The automatic balling gun of claim 7 wherein said elongated hollow member is cylindrical in shape.

11. The automatic balling gun of claim 7 wherein said portion of said rod comprises a reduced diameter portion spaced along said rod so that said reduced diameter portion aligns with said release assembly in said cocked position.

12. The automatic balling gun of claim 7 wherein said portion of said rod comprises a reduced diameter portion spaced along said rod so that said reduced diameter portion aligns with said release assembly in said cocked position.

13. The automatic balling gun of claim 1 where said elongated hollow member, said cap and said knob are non-metallic and said rod and release assembly are metallic.

14. The automatic balling gun of claim 7 where said elongated hollow member, said cap and said knob are non-metallic and said rod and release assembly are metallic.

15. The automatic balling gun of claim 1 wherein said stop is separable from said elongated hollow member.

* * * * *